(12) United States Patent
Kopelman et al.

(10) Patent No.: US 11,819,373 B2
(45) Date of Patent: Nov. 21, 2023

(54) SYSTEMS FOR PROVIDING FEEDBACK DATA USEFUL IN DENTAL PROCEDURES

(71) Applicant: ALIGN TECHNOLOGY, INC., San Jose, CA (US)

(72) Inventors: Avi Kopelman, Palo Alto, CA (US); Eldad Taub, Reut (IL)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 17/807,472

(22) Filed: Jun. 17, 2022

(65) Prior Publication Data
US 2022/0313413 A1 Oct. 6, 2022

Related U.S. Application Data

(60) Division of application No. 17/492,393, filed on Oct. 1, 2021, now Pat. No. 11,389,280, which is a continuation of application No. 17/079,035, filed on Oct. 23, 2020, now Pat. No. 11,135,045, which is a continuation of application No. 16/396,271, filed on
(Continued)

(51) Int. Cl.
| | |
|---|---|
| *A61C 19/04* | (2006.01) |
| *A61C 5/70* | (2017.01) |
| *A61B 5/00* | (2006.01) |
| *A61B 5/103* | (2006.01) |
| *A61C 13/00* | (2006.01) |
| *A61C 19/00* | (2006.01) |
| *A61C 9/00* | (2006.01) |

(Continued)

(52) U.S. Cl.
CPC ............ *A61C 19/04* (2013.01); *A61B 5/0002* (2013.01); *A61B 5/103* (2013.01); *A61C 5/70* (2017.02); *A61C 9/0053* (2013.01); *A61C 13/0004* (2013.01); *A61C 13/26* (2013.01); *A61C 19/00* (2013.01); *A61B 5/4547* (2013.01); *G16H 20/40* (2018.01)

(58) Field of Classification Search
CPC ....... H04L 9/3231; H04L 9/008; G06F 21/32; G06F 21/6245; G06N 3/0454; G06N 3/08; G06N 20/00; G06V 10/454; G06V 30/194
USPC ......... 713/186; 382/154, 128, 317; 345/419; 433/167; 600/476
See application file for complete search history.

(56) References Cited

U.S. PATENT DOCUMENTS

| | | | | |
|---|---|---|---|---|
| 2002/0180760 A1* | 12/2002 | Rubbert | ................. | G16H 50/50 345/630 |
| 2004/0136002 A1* | 7/2004 | Whaite | .................. | G01J 3/524 356/419 |

(Continued)

*Primary Examiner* — Kathleen Y Dulaney
(74) *Attorney, Agent, or Firm* — FISHERBROYLES, LLP

(57) ABSTRACT

An intraoral scanning system for scanning an intraoral dental structure of a patient in a dental procedure may include an intraoral scanner and one or more processors coupled to the intraoral scanner and programmed with instructions that when executed by the one or more processors cause the intraoral scanning system to build a 3D model of the intraoral dental structure of the patient based on scan data acquired via the intraoral scanner and output feedback on a display. The feedback may include highlighting a portion of the 3D model that includes scan data that includes a finish line of the intraoral dental structure, wherein the scan indicates that the finish line is not suitable for receiving a prosthetic.

10 Claims, 8 Drawing Sheets

Related U.S. Application Data

Apr. 26, 2019, now Pat. No. 10,813,734, which is a continuation of application No. 15/650,631, filed on Jul. 14, 2017, now Pat. No. 10,327,878, which is a continuation of application No. 14/288,255, filed on May 27, 2014, now Pat. No. 9,730,779, which is a continuation of application No. 12/954,791, filed on Nov. 26, 2010, now Pat. No. 8,858,231, which is a continuation of application No. 11/286,299, filed on Nov. 25, 2005, now Pat. No. 7,862,336.

(60) Provisional application No. 60/630,572, filed on Nov. 26, 2004.

(51) Int. Cl.
*A61C 13/271* (2006.01)
*G16H 20/40* (2018.01)

(56) References Cited

U.S. PATENT DOCUMENTS

| | | | | |
|---|---|---|---|---|
| 2004/0214128 | A1* | 10/2004 | Sachdeva | A61C 7/00 433/24 |
| 2004/0259057 | A1* | 12/2004 | Kim | A61C 9/0046 433/213 |
| 2006/0120582 | A1* | 6/2006 | Squilla | A61C 13/0004 382/128 |
| 2006/0263739 | A1* | 11/2006 | Sporbert | A61C 9/0053 433/213 |

* cited by examiner

SYSTEMS FOR PROVIDING FEEDBACK DATA USEFUL IN DENTAL PROCEDURES

RELATED APPLICATIONS

This application is a divisional of U.S. patent application Ser. No. 17/492,393, filed Oct. 1, 2021, now U.S. Pat. No. 11,389,280, issued Jul. 19, 2022, which is a continuation application of U.S. patent application Ser. No. 17/079,035, filed Oct. 23, 2020, now U.S. Pat. No. 11,135,045, issued Oct. 5, 2021, which is a continuation of U.S. patent application Ser. No. 16/396,271, filed Apr. 26, 2019, now U.S. Pat. No. 10,813,734, issued Oct. 27, 2020, which is a continuation of U.S. patent application Ser. No. 15/650,631, filed Jul. 14, 2017, now U.S. Pat. No. 10,327,878, issued Jun. 25, 2019, which is a continuation application of U.S. patent application Ser. No. 14/288,255, filed May 27, 2014, now U.S. Pat. No. 9,730,779, issued Aug. 15, 2017, which is a continuation application of U.S. patent application Ser. No. 12/954,791, filed Nov. 26, 2010, now U.S. Pat. No. 8,858,231, issued Oct. 14, 2014, which is a continuation application of U.S. patent application Ser. No. 11/286,299, filed Nov. 25, 2005, now U.S. Pat. No. 7,862,336, issued Jan. 4, 2011, which claims the benefit of U.S. Provisional Application No. 60/630,572, filed Nov. 26, 2004, each of which are incorporated herein by reference in their entirety.

FIELD OF THE INVENTION

This invention relates to a system and method for providing feedback information that facilitates and that may provide guidance for prosthodontic procedures in the intra oral cavity, i.e., procedures involving the installation and definition of dental prostheses. In particular, the invention relates to such systems and methods that are computerized.

BACKGROUND

Prosthodontics is the dental specialty concerned with artificial replacements of missing parts of the mouth and jaws, in particular of teeth and parts thereof.

In prosthodontic procedures designed to implant a dental prosthesis in the intra oral cavity, the dental site at which the prosthesis is to be implanted in many cases needs to be measured accurately and studied carefully, so that a prosthesis such as a crown or bridge, for example, can be properly designed and dimensioned to fit in place. A good fit is of the highest importance to enable mechanical stresses to be properly transmitted between the prosthesis and the jaw, and to prevent infection of the gums and so on via the interface between the prosthesis and the dental site.

In the prior art, the dental site is prepared by the dental practitioner, and a positive model of the site is constructed using known methods. Alternatively, the dental site may be scanned to provide 3D data of the site. In either case, the virtual or real model of the site is sent to the dental lab, which manufactures the prosthesis based on the model. However, if the model is deficient or undefined in certain areas, or if the preparation is not optimal for receiving the prosthesis, the dental technician has a more difficult job ahead than otherwise, and may result in less than optimal design for the prosthesis. In some circumstances, the model is rejected and the dental practitioner must re-scan the dental site, or must rework the preparation, so that a suitable prosthesis may be produced.

SUMMARY OF THE INVENTION

Herein, "dental material" refers to any material associated with dental structures of the intra oral cavity, including but limited to natural dental materials such as for example enamel, dentine, pulp, dental roots, and non-natural dental materials such as for example metallic and non-metallic filings, restorations, crowns, bridges, copings, preparations, and so on.

Herein, "dental clinic" refers to the interface between a dental practitioner and a patent, and thus includes any physical entity, in particular a clinic, in which there is interaction between a dental patient and a dental practitioner. While "dental practitioner" typically refers to a dentist, doctor or dental technician, it also includes herein all other caregivers that may interact with a dental patient during the course of a dental treatment. While "dental patient" typically refers to a person requiring the dental services of a dental practitioner, it also includes herein any person regarding whom it is desired to create a 3D numerical model of the intra oral cavity thereof, for example for the purpose of practicing the same or for carrying out research.

The term "prosthesis" is herein taken to include any restoration or veneering, including any onlays, such as crowns and bridges, for example, and inlays, such as caps, for example, and any other artificial partial or complete denture.

While the term "preparation" typically refers to the stump (including the finish line and shoulder) that is left of the tooth that is to be replaced by the prosthesis—typically a crown—and on which the crown is to be mounted, the term herein also includes artificial stumps, pivots, cores and posts, or other devices that may be implanted in the intraoral cavity in such a position or in a position that is optimal for implanting the crown.

The term "prosthodontic procedure" refers, inter alia, to any procedure involving the intraoral cavity and directed to the design, manufacture or installation of a dental prosthesis at a dental site within the intraoral cavity, or a real or virtual model thereof, or directed to the design and preparation of the dental site to receive such a prosthesis.

The term "numerical entity" is used herein synonymously with virtual model and other such terms, and relates to a virtual representation of a real object, typically a dentition or at least a part of intraoral cavity, or of a real model thereof, for example.

The present invention, in a first aspect thereof, relates to a method for providing feedback data useful in at least one prosthodontic procedure associated with the intra oral cavity, comprising:
 (a) providing at least one numerical entity representative of the three-dimensional surface geometry of at least part of the intra-oral cavity;
 (b) manipulating said entity to provide desired data of a type useful in at least a first said procedure;
 (c) determining at least one relationship between said desired data and said first procedure; and
 (d) generating feedback data representative of said at least one relationship.

Typically, in the said prosthodontic procedure, dental material has been previously removed from said part of the intra-oral cavity by means of a second procedure.

Optionally, step (c) comprises testing an adequacy of said desired data for performing said first procedure according to at least one predetermined parameter, and step (d) comprises generating feedback data representative of said adequacy.

The method is typically directed at a said first procedure comprising mounting at least one dental prosthesis with respect to a dental preparation comprised in said intraoral cavity and provided prior to step (a).

In a first embodiment of the invention, said desired data relates to the geometry of a finish line associated with said dental preparation. Step (c) receiving a prosthesis according to predetermined parameters; said feedback data in step (d) comprises a suitable message advising whether or not said finish line geometry is suitable, according to said determination in step (c). In step (c) it may be determined that the said finish line geometry is not suitable for receiving a prosthesis according to predetermined parameters, and in such a case the method may further comprise the step:

(e) providing suggested changes to said finish line geometry such as to provide a new finish line geometry that is suitable for receiving a prosthesis according to predetermined parameters.

The suggested changes may be calculated according to predetermined rules. Further, the suggested changes may be displayed on a two-dimensional representation of said dental preparation, wherein said new finish line geometry is superimposed over said representation. The location of said existing finish line geometry may be highlighted with respect to said new finish line geometry.

The method may further comprise repeating steps (a) to (d) after further material has been removed from the preparation to conform a finish line thereof to said new finish line geometry.

The method may further comprise repeating steps (a) to (d) concurrently with each step of a material removal operation, said material removal operation being adapted to conform a finish line of said preparation to said new finish line geometry, wherein step (e) is performed at each step of said material removal operation.

In a second embodiment, the desired data relates to an insertion path geometry for said prosthesis with respect to said dental preparation and surrounding dental tissues. Step (c) comprises determining whether or not the said insertion path geometry is suitable for enabling said prosthesis to be mounted with respect to said dental preparation. The feedback data may comprise a suitable message advising whether or not said insertion path geometry is suitable, according to said determination in step (c). In step (c) it may be determined that the said insertion path geometry is not suitable for receiving a prosthesis according to predetermined parameters, and the method may then further comprise the step:

(f) providing suggested changes to said dental preparation such as to provide a new insertion path geometry that is suitable for receiving a prosthesis according to predetermined parameters.

The suggested changes may be determined on the basis of identifying overlapping areas between the prosthesis and the preparation, and providing guidance as to corresponding changes required in at least one of said prosthesis and said preparation. Further, the suggested changes may be displayed on a two-dimensional representation of said dental preparation, wherein said new insertion path geometry is superimposed over said representation.

The method may further comprise repeating steps (a) to (d) after further material has been removed from the preparation to conform said preparation to said new insertion path geometry.

The method may further comprise repeating steps (a) to (d) concurrently with each step of a material removal operation, said material removal operation being adapted to said preparation to said new insertion path geometry, wherein step (e) is evaluated at each step of said material removal operation.

The prosthesis in the second embodiment of the invention is typically a crown or bridge.

In a third embodiment of the invention, the desired data relates to at least one predetermined dimension between said dental preparation and said prosthesis. Step (c) comprises determining whether or not the said at least one dimension is suitable for enabling a prosthesis to be received according to predetermined parameters. The at least one dimension typically relates to a characteristic thickness of said prosthesis. The said prosthesis may comprise a ceramic cap that is mountable over a metal coping bonded to said preparation, or a porcelain fused to metal (PFM) cap, for example.

The feedback data typically comprises a suitable message advising whether or not said at least one dimension is suitable, according to said determination in step (c). In step (c) it may be determined that the said at least one dimension is not suitable for receiving a prosthesis according to predetermined parameters, and further comprises the step:

(e) providing suggested changes to preparation geometry such as to provide a dimension that is suitable for receiving a prosthesis according to predetermined parameters.

The suggested changes may be determined taking into consideration the type of prosthesis to be implanted at said preparation. The suggested changes may be displayed on a two-dimensional representation of said dental preparation, wherein said changes to preparation geometry are superimposed over said representation.

Optionally, the method may further comprise repeating steps (a) to (d) after further material has been removed from the preparation to conform said preparation to said new preparation geometry.

Optionally, the method may further comprise repeating steps (a) to (d) concurrently with each step of a material removal operation, said material removal operation being adapted to conform said preparation to said new preparation geometry, wherein step (e) is evaluated at each step of said material removal operation.

For all embodiments, step (a) is typically performed by scanning said at least part of said intra oral cavity using a suitable 3D surface scanner.

According to a second aspect of the invention, in step (c) said relationship may be insufficiently determined due to incomplete definition of numerical entity provided by step (a). The method may then further comprise the step of determining the location of at least one area of said intra oral cavity where 3D definition thereof is required for enabling step (c) to be performed. Said determination of the location of said at least one area may be performed by suitable algorithms. The said at least one area is displayed on a two-dimensional representation of said dental preparation, wherein said at least one area is superimposed over said representation.

The prosthesis typically comprises any one of an inlay, onlay, crown, bridge or restoration.

Optionally, step (b) comprises simulating said procedure first with respect to said numerical entity to provide said desired data.

According to the second aspect of the invention, step (a) comprises the steps of:
scanning a part of said intra-oral cavity to provide a 3D numerical entity thereof;
determining whether a definition of said 3D numerical entity is sufficient for enabling step (c) to be performed;
if said definition is insufficient, advising a user to continue scanning a different part of said intra-oral cavity, and repeating step (ii) until said definition is sufficient, wherein step (v) is performed;

if said definition is sufficient in step (ii), proceeding with step (v);

advising a user that said definition is sufficient, and proceeding with steps (b) to (d).

Optionally, in step (a), said numerical entity further comprises color data of said part of the intra oral cavity, and step (b) comprises differentiating parts of said entity according to whether the said color associated therewith is correlated with soft tissues or hard tissues of the intra oral cavity.

Optionally, step (a) may be performed in one location, and at least one of steps (b) to (d) may be performed in at least one different location.

Optionally, step (d) is provided substantially in real-time with respect to step (a), or within a short time period thereof, typically in the order of seconds or fractions of a second.

According to the second aspect of the invention, a method of providing feedback data useful in at least one prosthodontic procedure associated with the intra oral cavity, comprises:

(i) providing at least one numerical entity representative of the three-dimensional surface geometry of at least part of the intra-oral cavity that has been previously modified by means of a first part of said procedure;

(ii) manipulating said entity to provide desired data useful in at least a second part of said procedure;

(iii) testing adequacy of said desired data for performing said second part of said procedure; and (iv) generating feedback data representative of said adequacy.

Typically, the first part of said procedure comprises a dental material removal operation in said intra-oral cavity. Further typically, step (ii) comprises manipulating said entity to determine sufficiency of definition of said numerical entity in step (i) with respect to said first said procedure, and providing sufficiency data representative of said sufficiency, and step (iii) comprises determining at least one relationship between said sufficiency data and said first procedure. In one application of the method according to the second aspect of the invention, the desired data may relate to a measure of surface data definition of said entity.

In the third aspect of the invention, the feedback data is essentially used in an interactive manner together with a material removing process to facilitate the performance of a procedure with respect to the intraoral cavity.

The present invention also relates to a system for providing feedback data useful in at least one prosthodontic procedure associated with the intra oral cavity comprising:

(A) scanner means for providing at least one numerical entity representative of the three-dimensional surface geometry of at least part of the intra-oral cavity;

(B) microprocessor means for manipulating said entity to provide desired data of a type useful in at least a first said procedure, and for determining at least one relationship between said desired data and said first procedure; and (C) output means for outputting feedback data representative of said at least one relationship generated by said microprocessor means.

The scanner may comprise a confocal scanner, for example. Preferably, the scanner comprises a capability for providing color data as well as geometrical data of a surface. Typically, the output means comprises a visual and/or audio display means. The microprocessor means is adapted for operation according to the method of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
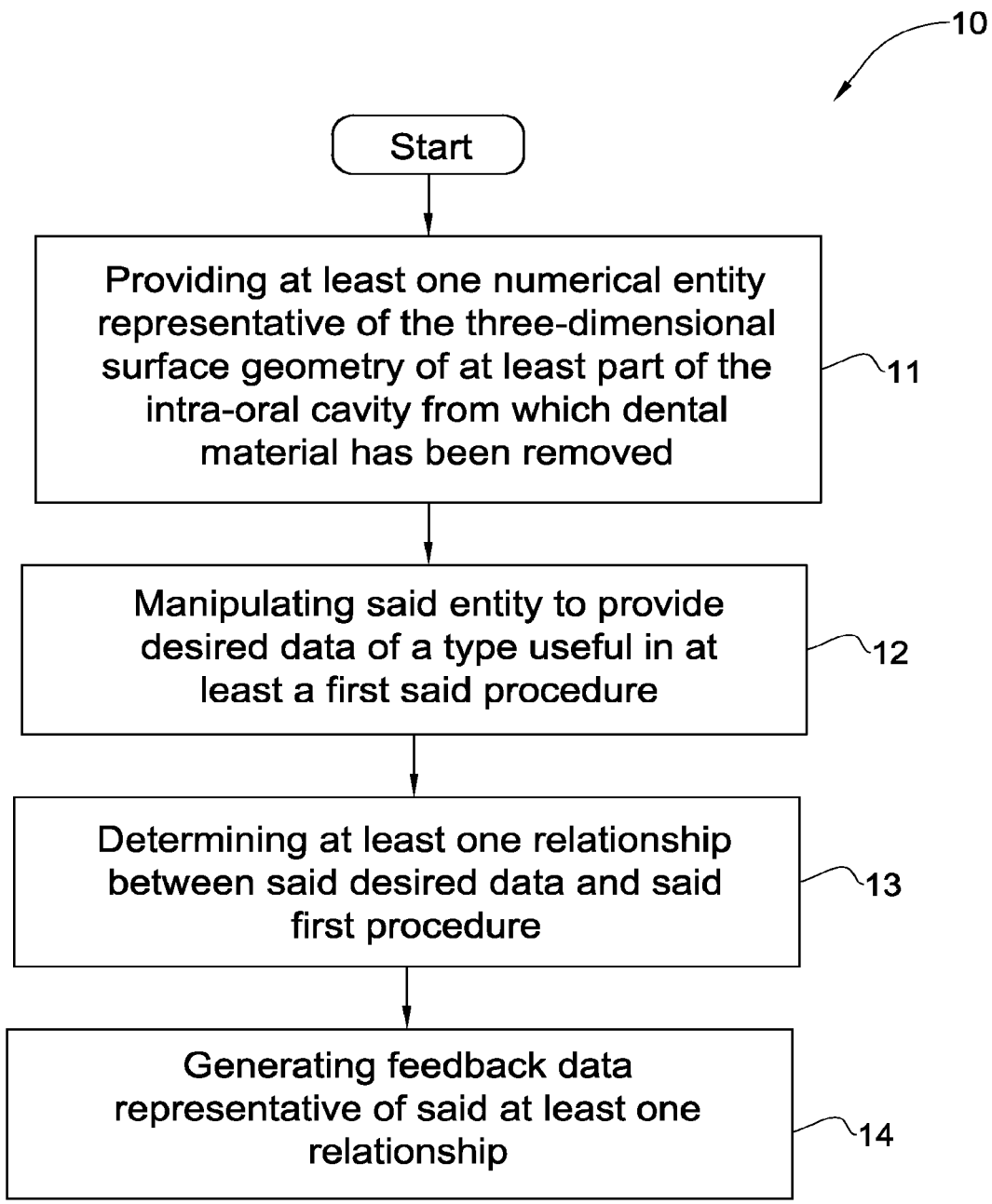
FIG. 1 is a block diagram illustrating steps of a method according to the first aspect of the invention.

FIG. 1 illustrates a method 10 for providing feedback data useful in at least one prosthodontic procedure associated with the intra oral cavity, in accordance with a first aspect of the invention. The method comprises the following basic 5 steps:

Step 11: providing at least one numerical entity representative of the three-dimensional surface geometry of at least part of the intra-oral cavity from which dental material has been removed.

Step 12: manipulating said entity to provide desired data of a type useful in at least a first said procedure.

Step 13: determining at least one relationship between said desired data and said first procedure.

Step 14: generating feedback data representative of said at least one relationship.

Thus, in the first aspect of the invention, the feedback data is essentially used to facilitate the performance of a prosthodontic procedure with respect to the intraoral cavity.

Preferably, steps 11 to 14 are carried out in a relatively short space of time, more preferably in real time or close thereto.

For all embodiments, the first step 11 of the method according to the present invention relates to providing at least one numerical entity that is representative of the three-dimensional surface. Tue said numerical entity is typically at least "three-dimensional", that is, each data point of the data set comprises at least three prime independent variables relating to spatial coordinates of a surface, typically defined along orthogonal Cartesian axes, x, y, z. Alternatively, these variables may be defined along polar axes or any other geometric system in which a surface may be described. Thus, the numerical entity typically comprises a data set having a plurality of at least 3-dimensional arrays—(x, y, z), wherein each array represents the x, y, z, geometrical coordinates.

Figure 2:
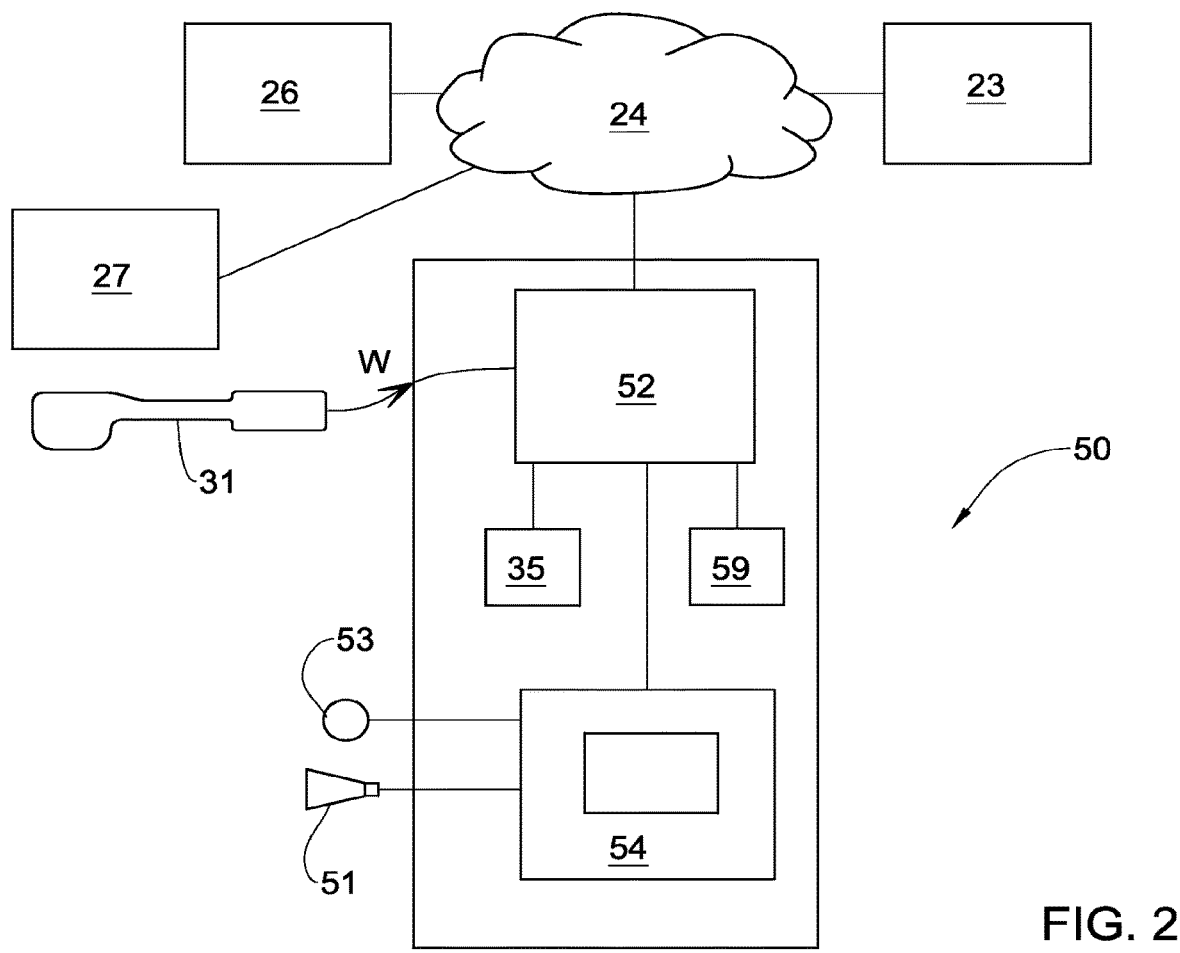
FIG. 2 is a block diagram illustrating elements of a system according to the present invention.

Any suitable means may be used to provide the numerical entity. FIG. 2 illustrates the main elements of the system 50 according to the present invention, comprising a suitable scanner 31, a microprocessor or computer 52, and a display means 54. According to the invention, digitized three-dimensional (3D) information W (FIG. 3) of the patient's intra-oral cavity, or part thereof, is created by the system 50 using scanner 31. Preferably, the 3D digitized data of the intraoral cavity is obtained, including the dentition and associated anatomical structures of a patient. The scanning means 31 may include, for example, a hand-held scanner that is used by the practitioner or other user to acquire the 3D data. Advantageously, a probe for determining three dimensional structure by confocal focusing of an array of light beams may be used, for example as manufactured under the name of PROSTHOCAD or as disclosed in WO 00/08415, the contents of which are incorporated herein in their entirety.

The system 50 is typically located at a dental clinic, and may be linked to one or more service centers 23 and/or dental labs 26, via a communication means or network such as for example the Internet or other suitable communications medium such as an intranet, local access network, public switched telephone network, cable network, satellite communication system, and the like, indicated by the cloud at 24. Optionally, it is also possible for some dental labs 26 to be linked to each other, via the same one or a different one of said communication medium, for example when such dental clinics or labs form part of a common commercial entity. Further optionally, such interlinked dental labs 26 may be further linked with other entities, for example a head clinic or head lab, comprising a centralized data base (not shown).

Typically, the design and manufacture of dental appliances for use in the intraoral cavity may be eventually carried out at the dental lab 26 or at the service center 23, or alternatively one or both of these activities may be shared between the two; in each case the design and manufacture are preferably based on the original 3D data of the oral cavity previously obtained. Thus, exchange of data between the system 50 and the dental lab 26 and/or service center 23 may be useful in creating an optimal geometry for a preparation being made in the intraoral cavity that enables the best prosthesis to be designed therefor, for example.

The dental lab 26 typically comprises a laboratory, or a design or manufacturing entity that may provide direct technical services to the dental clinic in which the system 50 is located. Such services may include, for example, scanning, manufacturing, analyzing the preparation in the intra oral cavity to mark the location of the finish line, for example, as disclosed in U.S. Ser. No. 10/623,707 and WO 04/008981, also assigned to the present assignee, and the contents of which are incorporated herein in their entirety, and so on. The dental lab 26 is typically characterized as being. equipped or otherwise able to design part or whole prostheses, and/or to partially manufacture or assemble the same, particularly where close tolerances are relatively less critical. On the other hand, while the service center 23 is also equipped to design part or whole prostheses, and/or to fully or partially manufacture and/or assemble the same, it is particularly suited to do any of these activities where close or tight tolerances are in fact critical and/or difficult to achieve.

While the service center 23 and dental labs 26 may be located in a different geographical zone to the dental clinic, for example, different countries, different cities in the same country, different neighborhoods in the same city, or even different buildings in the same neighborhood, they may also be housed in the same building, and in any case maintain their separate functions and capabilities, as described herein.

The system 50 may also be linked to one or more consultation centers 27, also via network 24, wherein such consultation centers 27 may comprise dental experts, for example, that may provide feedback data to the user of system 50, based on data transmitted therefrom to the centers 27, according to the invention.

According to the present invention, step 11 is carried out after a material removal operation has been applied to a part of the intra oral cavity. Such a material removal operation may be executed using any suitable machining tool that is adapted for material removal, and may include inter alia mechanical tools such as drills for example, laser tools such as for example laser drills or cutters, ultrasonic tools such as for example ultrasonic cutters, and so on. Alternatively or additionally, the material removal operation may comprise a loss of dental material, occurring, for example, via disease, mechanical forces such as a blow to the teeth for example, and so on.

Such a material removal operation may be directed for the purpose of, or may require, prosthodontic procedures, and may include the construction of a dental preparation at a dental site, so as to receive a prosthesis such as a crown, for example, or for providing a dental filling or restoration thereat.

Alternatively, the 3D digitized data may be obtained in any other suitable manner, including other suitable intra oral scanning techniques, based on optical methods, direct contact or any other means, applied directly to the patient's dentition. Alternatively, X-ray based, CT based, MRI based, or any other type of scanning of the patient's intra-oral cavity may be used. The dimensional data may be associated with a complete dentition, or of a partial dentition, for example such as a preparation only of the intra oral cavity.

Typically, the 3D digitized data is obtained in a manner such that enables the data to be procured from the patient and analyzed according to the invention during a regular visit of a patient to a practitioner.

Thus, advantageously, such a scanner 31 makes use of confocal imaging for providing an accurate three-dimensional representation of the target surface within the intraoral cavity.

Optionally, the numerical entity may further comprise a fourth prime independent variable, relating to a color parameter that is expressed numerically and is associated with the spatial coordinates. The color parameter may itself be comprised of independent prime color variables—for example relating to the red, blue and green (RGB) components associated with the color parameter. Alternatively, the color parameter may be expressed in terms of the Hue, Saturation and Intensity (HIS). Alternatively, any other color parameter may be used, including parameters that provide a measure of internal reflectance and translucency, or any other optical property of teeth. Thus, such a numerical entity typically comprises a data set having a plurality of 4-dimensional arrays—(x, y, z, c), wherein each array represents the x, y, z, geometrical coordinates, and wherein c represents the color value, of a point on a surface within the intra-oral cavity. Any suitable means may be used to provide this numerical entity. For example, a three-dimensional surface scanner with color capabilities may be used. Thus, advantageously, such a scanner makes use of confocal imaging for providing an accurate three-dimensional representation of the target surface within the intra-oral cavity. Color values may then be added to each data point of this data set by obtaining a two-dimensional color image of the target surface, and then mapping the color values of the two-dimensional image onto the three-dimensional "image", for example as described in co-pending applications assigned to the present assignee, U.S. Ser. No. 60/580,109, entitled "METHOD FOR PROVIDING DATA ASSOCIATED WITH THE INTRAORAL CAVITY", and U.S. Ser. No. 60/580,108, entitled "METHOD AND APPARATUS FOR COLOR IMAGING A THREE-DIMENSIONAL STRUCTURE". These references are incorporated herein in their entirety by reference thereto.

While only a limited number of embodiments of the present invention according to a first aspect are now described hereinbelow, it may be appreciated that the method of the invention may be used for a very wide variety of applications in which feedback data may be obtained for use in procedures associated with the oral cavity.

There are a number of exemplary procedures for which the method 10 is of particular utility. In one such example, the procedure relates to the provision of a prosthesis, such as a crown or bridge, for example, and inlays, such as caps, for example, and any other artificial partial or complete denture. In each case, an area in the intra oral cavity needs to be prepared for receiving the crown, bridge and so on. In the case of crown prosthesis, one tooth site needs to be prepared, while for a bridge prosthesis, two preparations need to be created, one at each of the abutment teeth for anchoring the bridge. Inlays require a different type of preparation at the tooth site.

Figure 4:
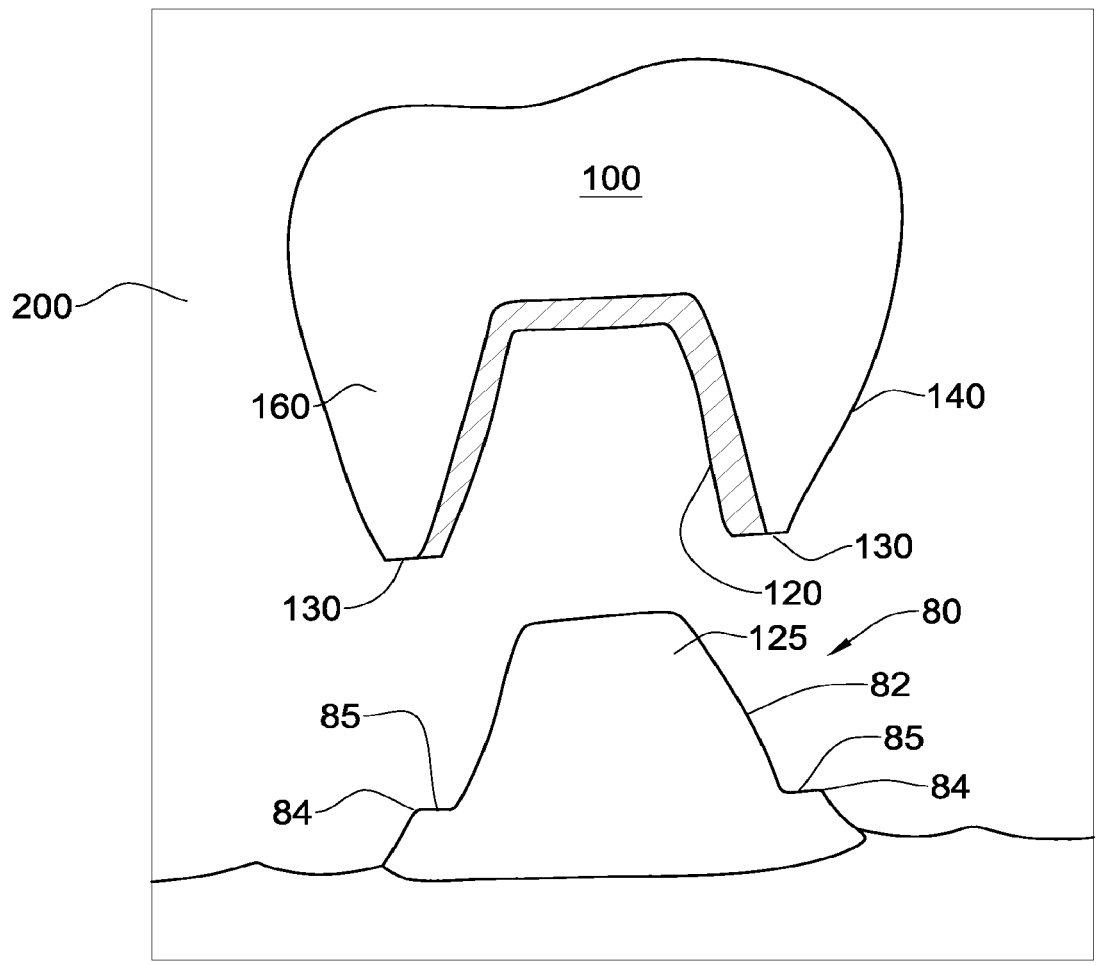
FIG. 4 illustrates a virtual crown prosthesis with respect to a virtual preparation area.

Referring to FIG. 4, a virtual representation of such a crown, generally designated 100, has an internal surface 120 and lower edge 130 that needs to be very precisely defined and manufactured to match the preparation 80 and finish line 84, respectively, in the intraoral cavity 200 of a patient. If the crown 100 is to comprise a coping 160, the said internal surface 120 is that of the coping 160.

Figure 3:
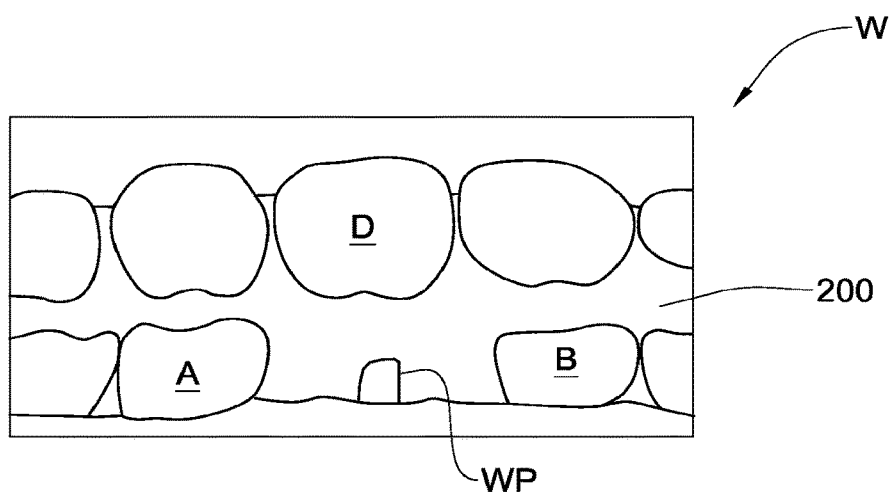
FIG. 3 illustrates a numerical entity of the intraoral cavity obtained with the system of FIG. 2.

The crown 100, which may be formed from a plurality of layers, preferably needs to have a natural looking appearance. Further, the dimensions of the crown 100, in particular the definition of the external surface 140 depends on external factors and needs to be such as to enable the crown 100 to fit between the adjacent teeth A, B, and to provide proper occlusion with the teeth D of the facing jaw (FIG. 3).

At the very least, the external surface 140 of the crown is such as to provide certain critical linear dimensions that comply with at least one of the target width or target height of a site or location on the jaw on which the crown is to be fitted. The target width may include the mesiodistal size of a tooth that is being replaced by the crown 100, and may be defined such as to provide adequate clearance between the crown 100 and adjacent teeth A, B, when the crown 100 is fixed onto the corresponding preparation in the intraoral cavity. The target height of the crown 100 may be defined such as to provide adequate occlusion with the "working side" of the tooth and avoiding interfering contact between the crown and teeth of the opposite jaw when the crown is fixed onto the corresponding preparation 80 in the intraoral cavity.

An outer shape for the external surface 140 may be chosen in a number of ways. For example, if the original tooth that the crown 100 is replacing is still available, and the outer surface thereof is of a reasonable form, this original tooth may be scanned and the 3D data of the surface obtained. If necessary, this 3D data may be considered as a starting point, and the final shape of the external surface 140 is obtained by manipulating this data as required by the technician or other user that is designing the surface 140. Alternatively, if the patient has a reasonably healthy tooth on the same jaw but on the adjacent quadrant at a position corresponding to where the crown is to be fitted, the 3D data of the surface of this tooth is obtained. Optionally, this tooth may be scanned as described herein to obtain the 3D spatial coordinates thereof, unless this data may already be available from the 3D data of the oral cavity 200 stored in the processor 52. Typically, such 3D-data would need to be transformed to provide a lateral inversion of the coordinates, suitable for a prosthesis in the other half of the jaw. Alternatively, a suitable profile for surface 140 may be chosen and obtained from a library 35 that comprises the 3D spatial profiles of shapes or profiles of the outer surfaces of a plurality of crowns and teeth. If necessary, the relative size and shape of the surface 140 may be adjusted by the user to better match the other teeth in the jaw. Then, the chosen surface is adjusted in any suitable manner, either manually, automatically, interactively or in any other manner, in order that the required target dimensions of surface 140 will fit within a control volume that defines the maximum dimensions of the crown 100, as required to conform to the space available in the intra oral cavity 200. In particular, the control volume may be chosen such as to provide adequate clearance between the crown and adjacent teeth, and adequate occlusion with the opposite teeth, when the crown 100 is properly fixed onto the preparation.

The processor 52 also has suitable software to define the inner surface 120 according to predetermined parameters. These parameters take into account the geometries of the external surface of the preparation 80 including finish line 84, the spacing required between the coping (if one is to be used with the crown) or the internal surface of the crown (if no coping is used) and the preparation to accommodate the adhesive or cement that is used to provide the bond between the two. The processor 52 may also comprise suitable software to provide the external shape of such a coping 160, and thus provide a complete geometrical representation or 3D data of the coping 160, digitally. The external surface of the coping 160 may be defined in any number of ways. Typically, at least a majority of the external surface of the stump 82 is displaced from the internal surface thereof by a uniform amount to provide an approximately constant thickness throughout. However, the thickness of the coping 160 may vary for a number of reasons. For example, it may be necessary in some cases to provide a coping that is stronger in some parts than in others, reflecting the activity that the crown 100 will be expected to engage in—as a molar, incisor, canine and so on.

The design of the external surface 140 and the internal surface 120 may be executed by the processor 52 at the dental clinic, or alternatively at the service center 23, or at the dental lab 26. If at the latter, and if use is made of a library of 3D spatial profiles of shapes or profiles of the outer surfaces of a plurality of crowns and teeth, then the dental lab 26 can make use of library of the service center 23, via communications network 24. Similarly, if the design is carried out at the dental clinic, the processor 52 may also make use of the library of the service center 23, via communications network 24. Alternatively, the system 50 may have its own digital library 35 of 3D spatial profiles of shapes or profiles of the outer surfaces of a plurality of crowns and teeth, operatively connected to a processor 52 or other computer, as illustrated in FIG. 2, which comprises display 54 and user interface 59 such as a mouse and/or keyboard.

Referring to FIG. 4, in a first embodiment of the invention, the method 10 is adapted for providing feedback data regarding the definition of the finish line 84. In particular, it is desired to receive such feedback data referring to the quality and clearness of the finish line 84, and optionally including the shoulder 85.

The finish line 84 may be of any type thereof, for example knife edge, feather edge, chamfer, chamfer bevel, shoulder, shoulder bevel, and so on. Alternatively, the finish line 84 may comprise a combination of different types around the periphery of the preparation, for example part of the finish line for a particular preparation may be knife edge, while another part may be feather edge.

Thus, having scanned the intraoral cavity 200, in particular the target zone T including the preparation 80, finish line 84 and (where appropriate) shoulder 85, the processor 52 then manipulates the resulting numerical entity W to identify the finish line 84. This may be done using any suitable algorithm. For this purpose, it may be advantageous for the entity W to also include color components for each surface point defined therein. The differentiation of dental surface color between the hard tissues and the soft tissues may be helpful in automatically defining the finish line, as described in the aforesaid co-pending application entitled "METHOD FOR PROVIDING DATA ASSOCIATED WITH THE INTRAORAL CAVITY". Generally, the shoulder type (e.g., porcelain shoulder, metal collar and so on) should match and be suitable for the prosthesis it is desired to implant at the dental site.

The geometry of the finish line 84 and optionally shoulder 85 may then be analyzed by the processor 52 according to predetermined rules, to establish the relationship between the virtual finish line thus identified, and the function which the finish line 84 and optionally shoulder 85 is to play in the mounting of the prosthesis to the preparation. Such rules may comprise, for example one or more of the following:
 (a) the finish line is continuous about the full periphery of the preparation;
 (b) the thickness of the shoulder 85, i.e., the radial dimension between the edge of the finish line 84 and the preparation 80, lies within a predetermined range;
 (c) the thickness of the shoulder 85 is substantially uniform along the periphery thereof;
 (d) there are no abrupt changes in slope of the finish line 84 along the periphery thereof;
 (e) the type of prosthesis to be implanted.

It may then be established by the processor 52 whether the finish line 84 and/or shoulder 85 comply with such rules, and can then provide feedback data to the user. Such feedback data may take many different forms. For example, in the positive, i.e., that the finish line, for example, is adequate, the processor 52 may be adapted to transmit a signal via display 54. Such a signal may be an audio or visual signal, such as for example the sound of a bell 51 of a particular frequency or a colored light source 53 such as a green light, which may light up and remain lit, or may blink, or the signal may be more complex, such as for example a message on a screen stating that the finish line is suitable.

In the negative, i.e., in cases where the finish line is not suitable according to the aforesaid rules, for example, the feedback data may first advise where the finish line is deficient. For example, if referring to the first rule listed above, there is a step or discontinuity along the periphery of the finish line, the location and extent of the same may be alerted to the user. For this purpose, a 3D representation of the preparation site may be displayed, with the part of the finish line in question highlighted in a different color to the rest of the finish line and/or of the preparation and so on. Similarly, if the practitioner is attempting to create a feather edge finish line (and this desire should be first inputted to the system 50 in an appropriate manner), deviations in geometry from this type of finish line—for example, part of the finish line is chamfered—may also be alerted to the user, for example by suitably annotating a graphical image of the preparation with colors and so on.

This also enables the practitioner to check whether the finish line is of the type he/she wants, or at least how close it is to this ideal.

Further, the feedback data may also comprise indications to the user as to where to modify the finish line 84 or shoulder 85 to achieve better results. In this context, an image of the numerical entity may be displayed in the display 54, with the finish line 84 and optionally also the shoulder 85 highlighted thereon. Then, the zones of the finish line that require further work may be contrasted with respect to the finish line 84 and/or the shoulder 85, for example by coloring such zones in a different color to the rest of the image. Optionally, zones may be colored differently according to the type of work required. For example, zones deficient with respect to rule (a) above may be colored in red, while those deficient with respect to rule (b) are colored in blue, and so on.

Thus, suggested changes to the finish line may be displayed on a two-dimensional representation of said dental preparation, via display 54, wherein said new finish line geometry may be superimposed over said representation.

Modification of the finish line 84 and/or shoulder 85 typically requires a material removing operation, and after doing so, the intra oral cavity 200 may be re-scanned to provide a second numerical entity. The second numerical entity, in particular the portions thereof relating to the finish line 84 or shoulder 85, may then be analyzed as before to determine whether the finish line 84 or shoulder 85 are acceptable according to the predetermined rules, and without reference to the original entity W. Alternatively, the second numerical entity may be compared with the original entity W, and any deviations between the two entities may be highlighted in display 54 in order to facilitate the next cycle of modification to the finish line.

Alternatively, the processor 52 may simply display the numerical entity and the highlighted finish line 84 and/or shoulder 85 on display 54, and this may at times represent sufficient feedback data for enabling the user to inspect the image thus created and to determine in a subjective manner whether the finish line and/or the shoulder are suitable or not. In all cases, the processor 52 is suitably programmed to enable the numerical entities to be viewed at any suitable angle and/or magnification.

Optionally, the numerical entity W may be transmitted to one or more remote locations, such as for example a service center of dental lab 26, to be analyzed there by a computer (not shown), or by a skilled technician or another user. The computer or skilled technician at the dental lab 26 may then communicate the results of the analysis to the original user via the communication network 24, or a different communication network, for example via cellular phone. These results may be in the form of numerical information that may be displayed, for example, or verbal instructions on how to proceed.

In a second embodiment of the invention, the method 10 is adapted for providing feedback data regarding the suitability of the preparation to accept a prosthesis of a predetermined type. Alternatively, the method 10 according to this embodiment is adapted for providing feedback data regarding the type of prosthesis that may be suitable for use with the preparation 80. In particular, it is desired to receive such feedback data referring to at least one predetermined dimension, such as for example a characteristic thickness of a prosthesis with respect to the geometry of the preparation and the adjacent teeth A and B.

Figure 5:
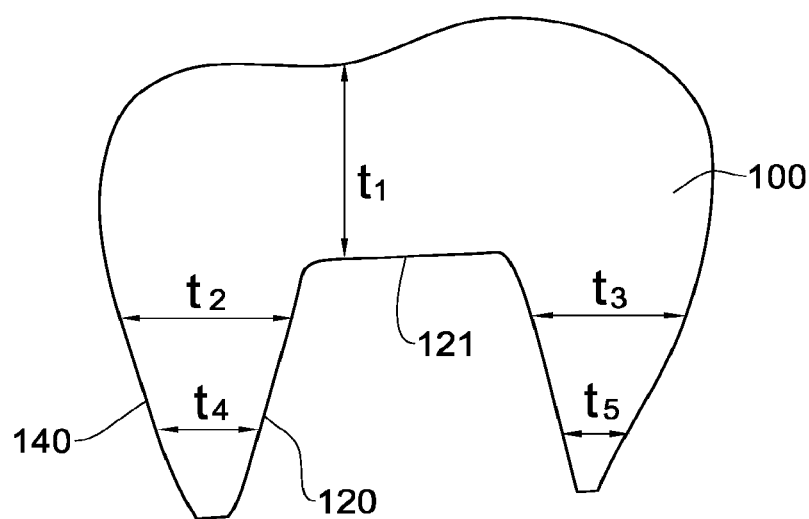
FIG. 5 illustrates dimensional parameters associated with the crown of FIG. 4.

Thus, having scanned the intraoral cavity 200, in particular the target zone including the preparation 80 and adjacent teeth A and B, as described above, mutatis mutandis, the processor 52 then manipulates the resulting numerical entity W to identify the external surface 125 of the stump 82 of preparation 80 (FIG. 4). This may be done, for example, by first identifying the finish line and optionally shoulder, for example as described above, and then isolating the coping surface enclosed by the perimeter defined by the finish line and/or shoulder. Then, an external crown surface 140 is chosen or designed for the crown, such as to fit properly in the space between the adjacent teeth A, B, as described hereinbefore. Then the relationship between the external surface 125 (which is typically closely correlated to the internal surface 120 of the crown 100) or of the internal surface 120, and the external surface 140 may then be analyzed by the processor 52 according to predetermined rules. This serves to establish the relationship between the thickness (referred to collectively herein as t) of the walls of crown 100, and the material from which the real crown (based on such a virtual crown 100) is to be produced as a function of the external surface 140 of the stump. Typically, such a relationship is dependent on the material from which the real crown is to be made. Referring to FIG. 5, such rules may comprise, for example one or more of the following:—
- the occlusal-gingival thickness $t_1$ between the apex 121 of the outer surface 125 (or of the inner surface 120) and the apex 141 of the crown 100;
- the mesial-distal thicknesses $t_2$, $t_4$, between the outer surface 125 (or of the inner surface 120) and the external surface 140 of the crown 100 at various occlusal-gingival distances;
- the labial-lingual thickness $t_3$ $t_5$, between the outer surface 125 (or of the inner surface 120) and the external surface 140 of the crown 100 at various occlusal-gingival distances. The suitability of the stump 82 itself may also be analyzed by suitable rules, to determine, for example, if it has sufficient mechanical strength to support the crown or other prosthesis thereon. For example, the volume of the stump and/or other critical thicknesses thereof may be determined by the processor 52. In another example, the stump may be analyzed to determine whether here are any discontinuities or undercuts that would provide insertion path problems, and these may be highlighted and brought to the attention of the user.

It may then be established by the processor 52 whether the geometry of the stump 82 complies with such rules, and can then provide suitable feedback data to the user. Such feedback data may take many different forms. For example, in the positive, i.e., that the stump 82 is adequate, the processor may be adapted to send a corresponding signal to display 54. Such a signal may be an audio or visual signal, such as for example the sound of a bell of a particular frequency or a colored light such as a green light, which may light up and remain lit, or may blink, or the signal may be more complex, such as a message on a screen stating that the finish line is suitable. Of course such a signal should be different from that provided with respect to the first embodiment described above, when both are available to the user.

In the negative, i.e., in cases where the stump 82 is not suitable according to the aforesaid rules, for example, the feedback data may comprise indications to the user as follows:—

To advise the user as to where to modify the stump 82 to achieve better results. In this context, an image of the numerical entity W may be displayed in the display 54, with the stump highlighted thereon. Then, the zones of the stump that require further work may be contrasted with respect to the stump 82, for example by coloring such zones in a different color. Optionally, zones may be colored differently according to the type of work required. For example, zones deficient with respect to rule (a) above may be colored in red, while those deficient with respect to rule (b) are colored in blue, and so on.

To advise the user that the stump 82, as is, provides a crown thickness that is too thick, and that therefore a filing composition needs to be added at least to some portions of the stump. The display 54 can then show where to add the composition, and when this is done, the intra oral cavity 200 may be rescanned to determine how and where to modify the stump. Alternatively, if the stump 84 is totally unsuitable the processor 52 provides a suitable signal to be displayed by display 54, and it may be necessary to replace the stump 84 with a pivot, core or post.

To advise the user that although the stump is unsuitable for use with a prosthesis made from one material (predefined), it may be suitable if the stump is made from a different material. For example, a stump made from PFM (Porcelain Fused Metal) can be thinner than a whole ceramic crown. Therefore, if a PFM crown was originally decided upon, it may be advisable to switch to a whole ceramic crown, and the processor 52 can determine whether the stump 82 would be suitable for such a crown.

Optionally, a contour or occlusion map of the target zone T may be provided, for example as disclosed in U.S. Pat. No. 6,334,853 and EP 0984739, the contents of which are incorporated in their entirety herein, and which references are also assigned to the present assignee. Such a dental occlusion map is indicative of distances between opposite regions on facing surfaces of opposite dental surfaces of the upper jaws of the mouth, for example the preparation 80 and the opposed tooth D. The occlusion map may be created by manipulating the entity W so as to determine the distances between opposite. regions on the opposite dental surfaces of the upper and lower jaws of the target zone T, and then setting up a correspondence between the determined distances and regions on a mapping surface. Accordingly, it is possible to provide, for example, a colored contour map showing the occlusion distances with respect to the preparation 80, for example, and from this determine whether and what parts of the preparation require further work, or whether there is preparation adequacy or preparation clearance regarding the worked target zone T. In particular, the occlusion map may inform the practitioner whether the preparation is adequate for the type of crown that he/she was intending to use, or what type of crown may be used, if any, with the preparation in its present condition. For example, a PFM crown typically requires greater occlusion between the preparation and opposed tooth (due the requirement for greater material thickness) than an all-ceramic crown, which in turn needs more clearance than a metal crown.

Optionally, the system 50 may be configured for automatically advising whether, for a given desired type of prosthesis (for example ceramic, PFM, metal and so on) the preparation is adequate, or conversely, given the current state of the preparation, what is the optimal type of prosthesis that is best suited for it, or if in fact the preparation is still unsuitable for receiving any prosthesis in its current state. This feature allows the practitioner to check whether the preparation is of the type that he/she wants. Further, the system 50 may be adapted to provide the practitioner with indications on how to further work the preparation so that it is optimally suited to the type of prosthesis that it is desired to be used therewith. For example, the contour map and/or a graphical representation of the target zone T may be annotated, for example by suitably coloring corresponding areas therein, to indicate the corresponding areas of the preparation where more material needs to be removed, for example, as to accommodate a particular type of prosthesis.

Modification of the stump 82 typically requires a material removing operation, and after doing so, the intra oral cavity may be re-scanned to provide a second numerical entity. The second numerical entity, in particular the portions thereof relating to the stump 82, may then be analyzed as before to determine whether the geometry of the stump 82 is acceptable according to the predetermined rules, and without reference to the original entity. Alternatively, such a second numerical entity may be compared with the original entity, and any deviations between the two may be highlighted in display 54 in order to facilitate the next cycle of modification to the stump 82.

Alternatively, the processor 52 may simply display the numerical entity and the highlighted stump 82 on display 54, and this may at times represent sufficient feedback for enabling the user to inspect the image thus created and to determine in a subjective manner whether the stump 82 is suitable or not.

Optionally, the numerical entity may be transmitted to a remote location such as for example a dental lab 26, to be analyzed there by a computer (not shown), or by a skilled technician or another user. The computer or skilled technician may then communicate the results of the analysis to the original user via the communication network 24 to provide feedback data to the original user regarding the stump 82.

In a third embodiment, the method 10 is adapted for providing the user with feedback data regarding the insertion path with respect to a preparation or preparations that is/are being created at a dental site for receiving a prosthesis such as a crown or bridge.

Taking the relatively simpler case of a crown first, the method 10 comprises the first step of providing a numerical entity of the intraoral cavity, including in particular the part of the cavity comprising the preparation. Optionally, and preferably, the numerical entity also comprises 3D data of the teeth A, B adjacent to the preparation 80. The 3D numerical entity may be provided in a similar manner to that described herein, mutatis mutandis.

In the next step, it is desired to determine whether the preparation is suitable to receive a crown prosthesis. One aspect of such a determination is to advise the user whether the preparation 80 provides an adequate insertion path for the crown. In this connection, the processor 52 first identifies from the entity W the external surface 125 corresponding to the part of the preparation onto which the crown is to be mounted (FIG. 4), and suitable algorithms for this purpose may be created, possibly as described above for the second embodiment, mutatis mutandis. Then, a virtual model 100 of the crown is either created by the processor 52, or input thereto by the user or a third party such as service center. or dental clinic 26, for example. Alternatively, this process may be commenced with a virtual model of the coping 160. The crown model 100 must be sized such as to fit between the adjacent teeth A, B, and thus be in abutting contact therewith when properly mounted onto the preparation 80. The crown model 100 may be a full 3D model, comprising an external 3D surface, or may simply comprise key dimensional parameters, such as for example the mesiodistal width of the tooth between the adjacent teeth A, B. The crown model 100 also comprises a full 3D representation of the internal 3D surface 125, which may be substantially complementary to the external surface 120 of the preparation, optionally taking into account an adhesive layer thickness that is to be introduced between the preparation and the said internal surface. The processor 52 then calculates the insertion path for the internal surface 120 of the virtual crown 100, and then checks whether this path is also suitable for the external surface 140 of the virtual crown 100. Alternatively, the processor 52 calculates the insertion path for the external surface 140 of the virtual crown 100, and then checks whether this path is also suitable for the internal surface 120 of the virtual crown 100. Ideally, the insertion path of the virtual crown 100 as a whole should enable the same to be maneuvered into position with respect to the preparation without colliding with or unduly interfering with other dental surfaces at or in the vicinity of the preparation.

Figure 6:
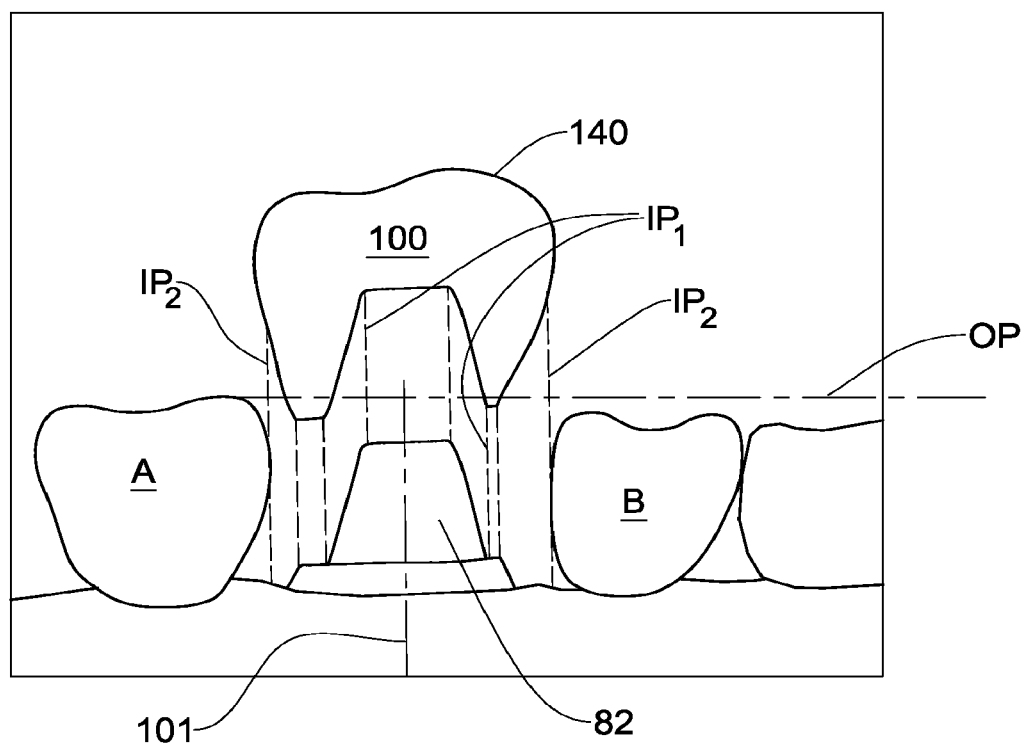
FIG. 6 illustrates the insertion path for a crown prosthesis with respect to a preparation.
Figure 7:
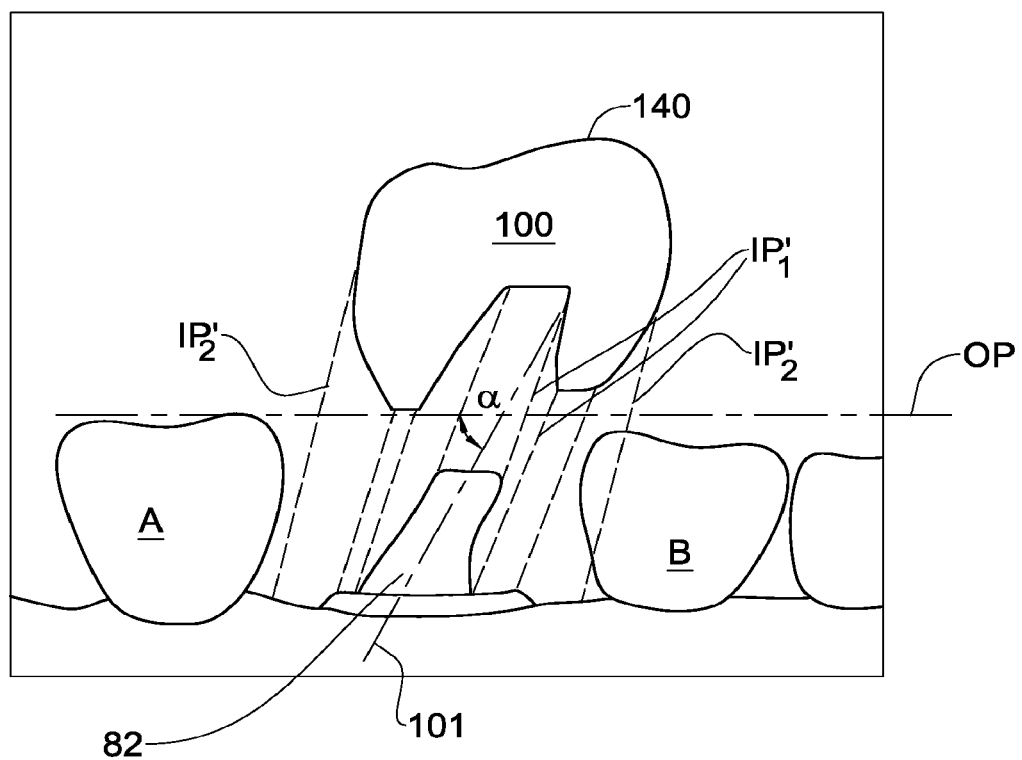
FIG. 7 illustrates the insertion path for another crown prosthesis with respect to a preparation, constrained to follow the insertion path defined by the internal surface of the prosthesis.

For example, referring to FIG. 6, the geometry of the preparation 82 approximates a right frustro-conical cone, and the central axis 101 thereof is more or less perpendicular to the occlusal plane OP. In this example, the insertion path $IP_1$ of the internal surface constrains the external surface 140 to path $IP_2$, which enables the external surface of the virtual crown 100 to be guided to the mounted position on the preparation without interfering or colliding with other parts of the dentition. In the Example illustrated in FIG. 7, the geometry of the preparation is approximately that of a slanting frustro-convex cone, wherein the central axis 101 thereof is at a minimum angle a to the occlusal plane. In this example, the insertion path $IP_1'$ of the internal surface constrains the external surface to path $IP_2'$, which would result in the external surface 140 of the virtual crown 100 colliding with adjacent tooth B, and it would be impossible to fit a real crown corresponding to the virtual crown 100 with such a preparation geometry. Similarly, in the example illustrated in FIG. 8, the insertion path $IP_2''$ of the external surface constrains the internal surface to path $IP_1''$, which would result in an undercut part 105 of the virtual crown 100 colliding with the stump 82, and it would be impossible to fit a real crown corresponding to the virtual crown 100 with such a preparation geometry. Optionally, the overhanging portion 88 and/or undercut part 105 may be highlighted by suitably coloring the corresponding zone in a graphical representation of the target zone T.

Figure 8:
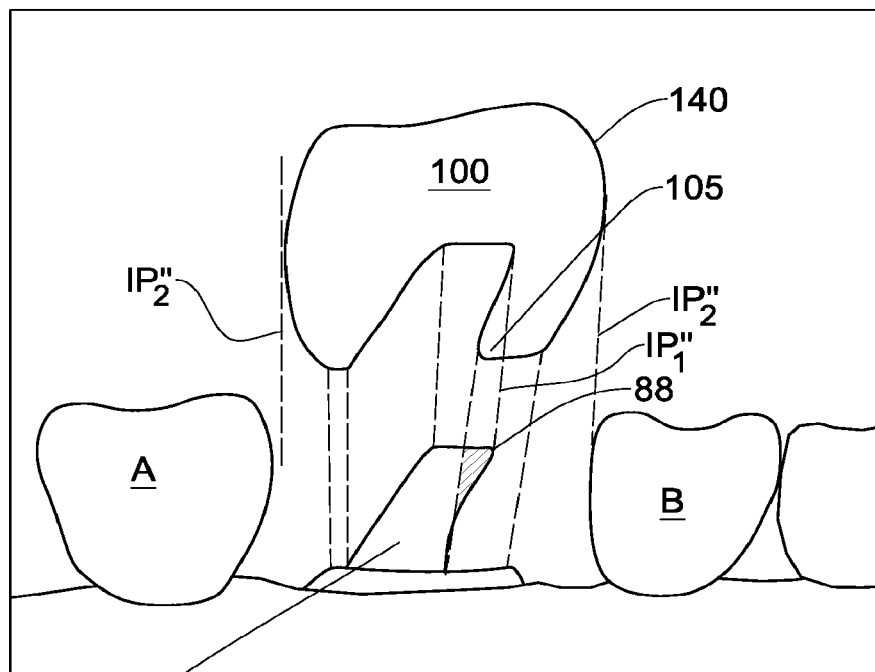
FIG. 8 illustrates the insertion path for the prosthesis of FIG. 7 with respect to a preparation, constrained to follow the insertion path defined by the external surface of the prosthesis.
Figure 9:
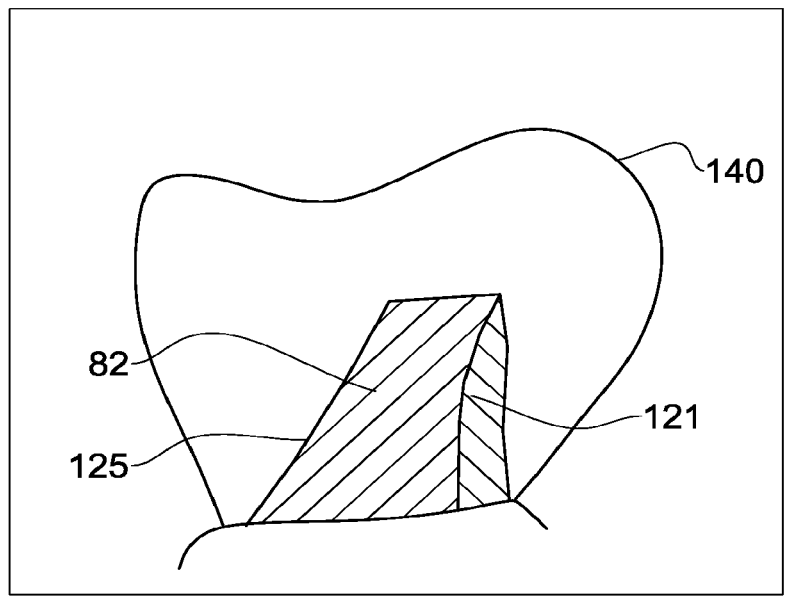
FIG. 9 illustrates an auxiliary prosthesis for use with the preparation stump having an undercut.

Optionally, and particularly when the geometry of the preparation is similar to that shown in FIG. 8, another type of plan may be considered in place of or in conjunction with a material removal plan. Having a slanting frusto-conical profile for the preparation typically requires material to be removed until a substantial part of the overhanging portion 88 of the stump 82 is removed. Such a procedure may result in over-weakening of the stump 82. Instead, and according to the invention, it is possible to create an internal surface of the virtual crown 100 that is not fully correlated to the external surface 125 of the stump 82, but only partially correlated thereto, along areas thereof that are non-overlapping in the direction of the insertion path, e.g., in which there is no undercuts. However, regarding the overlapping areas of the stump 82, i.e., the part of the stump overshadowed by the overhanging portion 88 in the direction of the insertion path, it is instead possible to create a portion of the internal surface 120 of the crown 100 corresponding thereto that is designed not to interfere or in any way collide with the overlapping areas of the stump 82 when the same is installed via the appropriate insertion path. The overlapping areas or zones refer to portions of the crown 100 which would need to be removed to prevent collision of the internal surface 120 of the crown 100 with the stump 82. However, this would leave a substantial cavity between the part of the preparation and the corresponding part of the internal surface of the crown. This cavity is preferably filled by manufacturing an auxiliary prosthesis 121 having the shape of this cavity, and then bonding the auxiliary prosthesis to the stump 82, as illustrated in FIG. 9. Alternatively, suitable cement or filler material may be bonded to the overlapping areas, and these areas then subjected to a material removal operation to provide the desired result. Particularly in such a case, but also for the previous case in which an auxiliary prosthesis for the cavity is bonded in place, the modified stump may be scanned to check the new geometry of the modified preparation.

The insertion paths for prostheses are preferably substantially rectilinear, to ease the user's task in duplicating the path when maneuvering the real crown onto the preparation. However, it is also possible to calculate insertion paths in which there is one or more change in the direction thereof, and/or in which the crown (i.e., first the virtual crown, and then the real crown) can be rotated about one or more of three orthogonal axes.

In some cases, there may be a plurality of possible insertion paths for the internal surface, or particularly for the external surface, and the processor 52 can attempt to match such paths.

When more than one matching pair of internal and external insertion paths match, the various alternatives may be presented to the user by means of display 54. Additionally or alternatively, the processor 52 may determine which matching pair is optimal, based on rules, or may present the different options in ascending or descending order of preference, according to any predetermined criteria, such as for example requiring a minimum number of direction or rotational changes in the path.

Preferably, display 54 displays an image of the dental site 200, together with the predicted insertion path of the internal surface and that of the external surface constrained thereby, or vice versa, and the processor 52 also provides the necessary input to the display 54 to highlight any part of the adjacent teeth A, B and/or preparation 80 that interfere with the particular insertion path. Alternatively, or additionally, when a situation such as those illustrated in FIGS. 7, 8 arises, the processor 52 may generate a suitable warning signal, audio and/or visual, warning the user that the insertion path for the current preparation geometry is not suitable, and that remedial action is required.

In particular, the processor may be programmed to determine possible plans for removing additional dental material from the preparation 80 to enable a suitable insertion path to be provided. This may be accomplished in a number of ways. For example, the processor may determine a particular suitable path for the external surface 140 of the virtual crown 100, for example the simplest and most direct path, and then identify the zones of the preparation which would need to be removed to prevent collision of the internal surface of the crown therewith, herein referred to as the "overlapping zones". However, since the internal surface of the crown is a function of the external geometry of the preparation, this procedure is preferably accomplished in a reiterative manner. That is, once the processor 52 identifies the overlapping zones, and removes, in a virtual manner, a small part of the overlapping zone. The amount of removal may be preset by the user, and any increment is possible. Preferably, such an amount may be correlated to the minimum removal of material that is normally possible in an analogous real life situation. The processor 52 then adjusts the geometry of the internal surface of the virtual crown 100 to take into account the new preparation geometry, and examines the insertion path of the inner surface with respect to the new preparation geometry. If there is still interference between the internal surface and the preparation, more material is removed in the virtual sense, the geometry of the internal surface 120 adjusted, and the new internal surface insertion path re-examined for collision. Additional cycles may be performed until the external surface 125 of the preparation is suitably modified to be compatible with the insertion path.

In some cases, the result of such a virtual procedure may not be acceptable for a real crown, for example too much material needs to be removed, and this would provide a much weakened stump 82, according to pre-known rules.

Accordingly, the virtual procedure may be repeated, each time starting with a different insertion path for the external surface 140, until a reasonable preparation geometry is arrived at that is compatible with the external insertion path and that is also reasonable according to such rules.

Additionally or alternatively, other virtual procedures for modifying the geometry of the preparation may be accomplished. For example, such a procedure may involve a combination of reducing the overhanging portion, and adding an auxiliary prosthesis 121.

However, it may be possible, that, given the condition of the preparation and the topology of the adjacent dental surfaces, no reasonable modified preparation geometry can be found. Such an outcome is also feedback data that is presented to the user.

Thus, the geometry of such a preparation is optionally, and preferably, analyzed according to such rules, and a suitable warning provided to the user when the geometry of preparation is inherently unsuitable. The warning may be audio/and or visual, and may be simple, such as a bip or series of bips, or a flashing light or lights, or may be complex for example an audio or a visual message, created by the processor 52, actually describing the reason for the warning. For example, such a warning could comprise an audio and/or visual message stating "Warning! The stump geometry is defective!". Where such warnings are audio, the display 54 preferably comprises optional earphone or headphones that enable the user to hear the message, but not the patient, since such a message may cause unnecessary alarm or anxiety to the patient. Such earphones or headphones may be operatively connected to the processor 52 via suitable cables, or via remote link such as an infrared transmitter/receiver system, or may be integrated into display 54, for example. A similar analysis and warning, where necessary, may be provided at the beginning of the exercise, and thus alert the user that the original preparation is unsuitable, preferably listing the reasons. In either case, where the present or virtually modified preparation is inherently unsuitable, the processor 52 may be programmed to provide recommendations, such as to remove the preparation completely, and to replace it with a pivot core or post.

On the other hand, if the processor 52 determines one or more material removal plans for the preparation 80 which theoretically yield a reasonable preparation geometry compatible with a possible insertion path, the different plans may be displayed to the user, who can the choose one plan. Preferably, each plan comprises displaying the overlapping areas of the preparation that require to be modified; and the nature of the insertion path that is required for maneuvering the prosthesis into place. Both factors need to be weighed by the user before deciding how to proceed. The aforementioned overlapping areas can be displayed over an image of the dentition (provided from the 3D entity W), and preferably such an image can be manipulated, for example on a screen, to enable the user to fully study the plan.

Once a preparation modification plan is chosen, the user can modify the real preparation area in the intraoral cavity as closely as possible to the overlapping areas marked in the virtual model (3D numerical entity). At any point in the material removal procedure, the user may re-scan the intraoral cavity to check on the progress. For this purpose, the processor 52 may be further programmed to effectively overlay the new numerical entity over the original entity, in particular to highlight the differences in geometry between the areas in which actual material removal has occurred and the overlapping areas which were earmarked by the procedure for material removal. Further, the processor 52 may be further programmed to detect with respect to these entities where material still needs to be removed, and where too much material has been removed. This may be displayed in display 54 on an image of the intraoral cavity, and the under-modified areas may be displayed in one color, say green, and then over modified areas may be displayed in a different color, say red. Preferably, should the presence of over-modified areas be detected, i.e., areas where too much material has been removed, the processor 52 recalculates the insertion path and advises the user whether the original modification plan is still possible, or whether the excess material removal requires a modification of the plan. Such a modification in the plan may be determined in a similar manner to the original plan, as described above, mutatis mutandis. Of course, it is also possible that the over modified areas have now rendered the preparation unsuitable according to the aforementioned rules, and the preparation must be replaced with an artificial pivot, core or post.

The methodology described above for an insertion path has been described with respect to a crown that is directly bonded onto a preparation, such as for example a metallic crown. For other types of crowns (for example ceramic crowns) that require a coping, the method is modified to take account of the coping geometry. Thus, the external surface 125 of the stump is displaced outwardly to create a virtual representation of a constant thickness coping. Alternatively, any other suitable means may be used to define the coping external surface. The internal surface 120 of the crown is then defined with respect to the external surface of the coping, and is typically complementary thereto, optionally taking into account a thin layer of adhesive.

The above method may also be adapted for the purpose of providing a suitable insertion path for the coping itself, mutatis mutandis.

Figure 10:
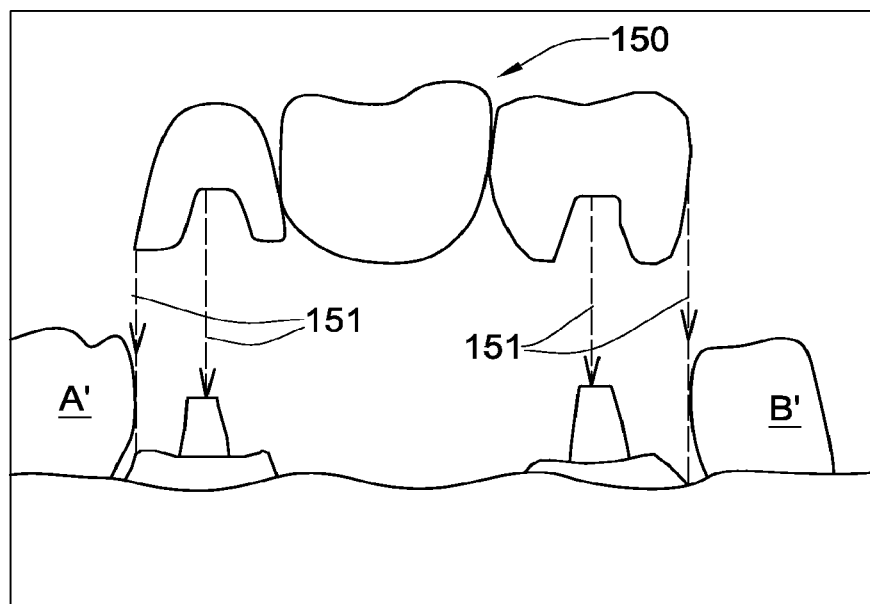
FIG. 10 illustrates a bridge prosthesis having a suitable the insertion path with respect to a preparation.
Figure 11:
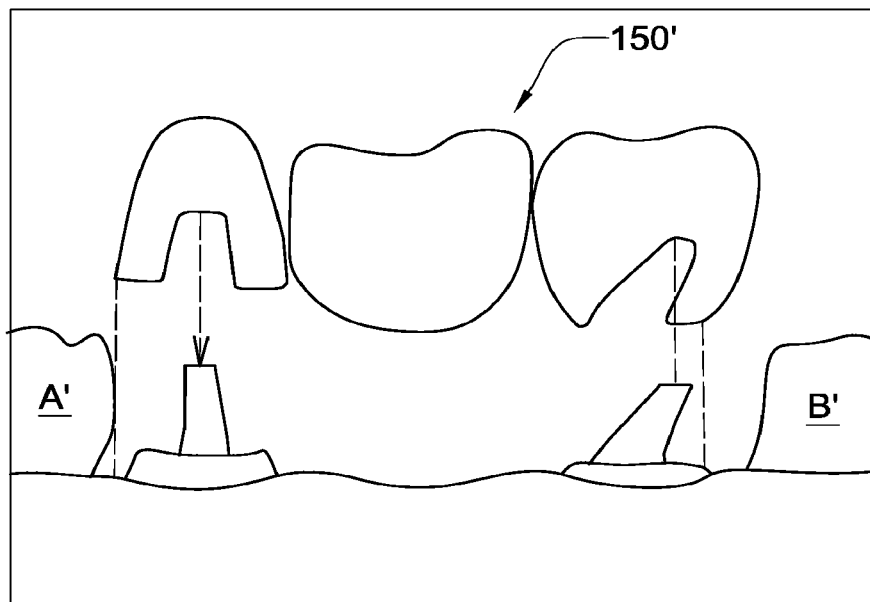
FIG. 11 illustrates a bridge prosthesis having a non-suitable insertion path for with respect to a preparation.

The methodology described above for the insertion path of a crown may be used, mutatis mutandis, for any dental restoration or dental prosthesis. In the case of a bridge, in particular, preparations have to be created in the abutment teeth on 5 either side of the missing tooth, and the geometries of both preparations need to be considered simultaneously in relation to the :insertion path of the bridge as a unit. Thus, referring to FIG. 10, the preparation geometries illustrated allow the bridge 150 to be mounted via an insertion path 151, while the preparation geometries illustrated in FIG. 11 do not provide a common insertion path for the bridge 150'. Thus, in order for the insertion path for the bridge 150 to be suitable, the individual insertion paths for the two preparations must be parallel, and moreover, such an insertion path must be such as to avoid collision of the bridge with the adjacent teeth A' and B'. In the analysis and design of modification plans for such cases, the processor 52 may provide one or more plans for the modification of one or both of the preparations, substantially as described above for a crown, mutatis mutandis. While the cases illustrated in FIGS. 10 and 11 relate to a 3-unit bridge, the aforegoing relates, mutatis mutandis, to a multiple unit bridge as well.

Figure 12:
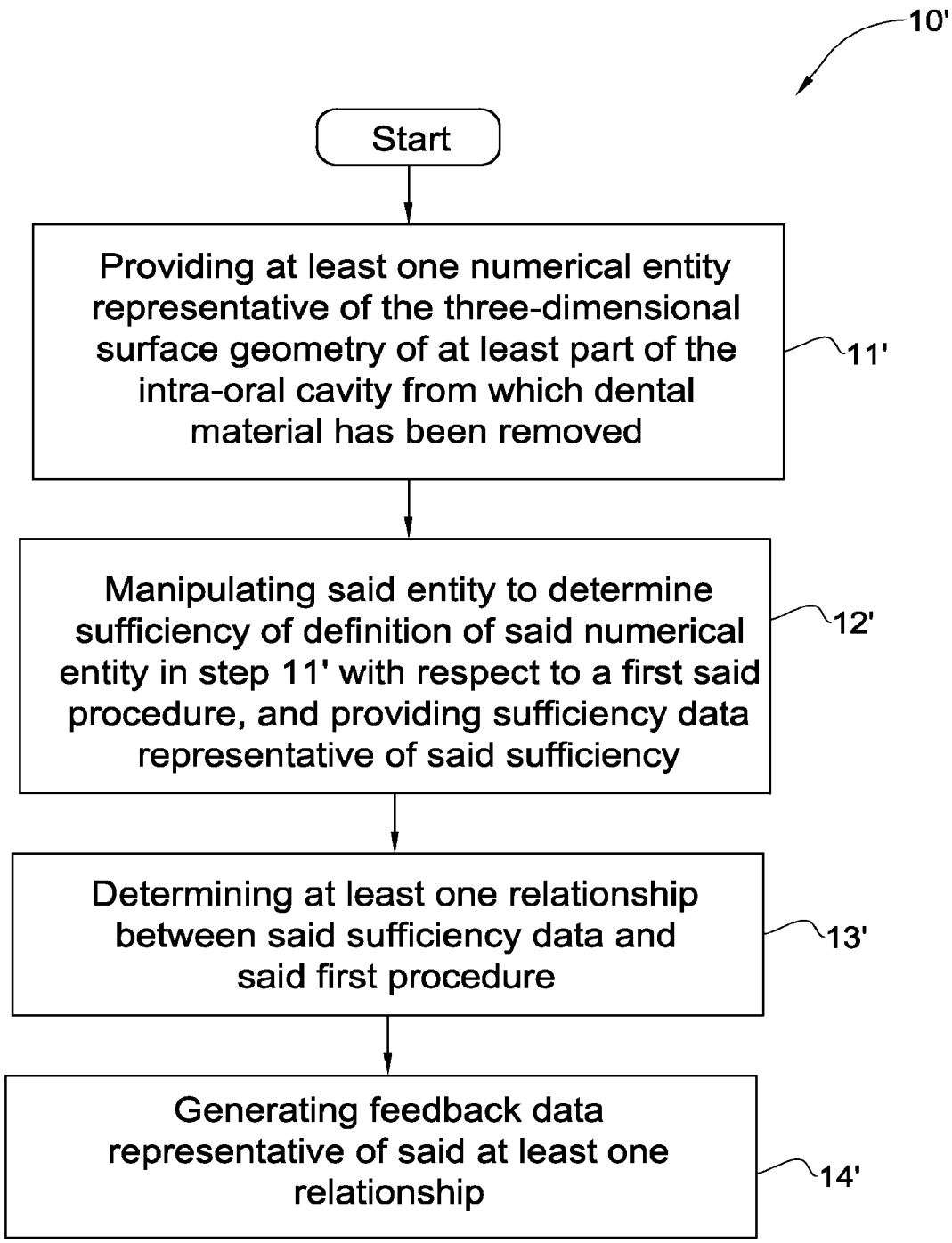
FIG. 12 is a block diagram illustrating steps of a method according to the second aspect of the invention.

The FIG. 12 illustrates a method 10' for providing feedback data useful in at least one prosthodontic procedure associated with the intra oral. cavity, in accordance with a second aspect of the :invention. In the second aspect of the invention, the method is concerned with ensuring that numerical entity W sufficiently defines the area of interest of the intraoral cavity. The method 10' comprises the following basic steps:

Step 11': providing at least one numerical entity representative of the three-dimensional surface geometry of at least part of the intra-oral cavity from which dental material has been removed.

Step 12': manipulating said entity to determine sufficiency of definition of said numerical entity in step 11' with respect to a first said procedure, and providing sufficiency data representative of said sufficiency.

Step 13': determining at least one relationship between said sufficiency data and said first procedure.

Step 14': generating feedback data representative of said at least one relationship.

Preferably, steps 11' to 14' are carried out in a relatively short space of time, more preferably in real time or close thereto.

For all embodiments, the first step 11' of the method according to the present invention relates to providing at least one numerical entity that is representative of the three-dimensional surface. This step is carried in a similar manner to step 11 of FIG. 1, as described above, mutatis mutandis.

Thus in step 11', scanner 32 of system 50 (FIG. 2) scans the area of interest of the intraoral cavity and a numerical entity corresponding to the surface scanned is created by processor 52 and optionally displayed by display 54. As with the first aspect of the invention, the data from the scanner may be transmitted to a dental clinic 23, service center 26, or consultancy center 27, inter alia, for creation of the numerical entity, which is then transmitted to the processor 52.

In step 12', the processor 52 (or indeed another computer in the aforesaid dental. clinic 23, service center 26, or consultancy center 27, inter alia) analyses the numerical entity to determine the sufficiency of definition of the numerical entity. The numerical entity may be obtained in a single scan, or alternatively, the numerical entity is originally created by taking multiple scans of the target area, and stitching the numerical entities thus obtained together. In any case, the processor 52 first checks whether the numerical entity lacks surface data in any particular part thereof. Such a lack of data may be due to the user not passing the scanner over the full zone to be scanned, for example, or by taking multiple scan in which there is insufficient overlap, for example.

When multiple scan are employed, then, in step 11', the scanner 31 may be used for obtaining high resolution numerical sub-entities representative of the surface topography within the intra-oral cavity. Accordingly, different zones of the intraoral cavity are sequentially scanned with scanner 31 to provide the corresponding sub entities. Some of these zones typically partially overlap with all the other zones, while other zones may only overlap with one or two other zones, and thus theoretically the corresponding sub-entities should have a portion of their data identical to one another within the overlap zone. However, since the scanner itself moves in orientation and position from scan to scan, the coordinates relating to these overlap zones will usually vary between adjacent scans, even though they relate to the same spatial feature. Nevertheless, by identifying the overlap zone within the entities, the spatial relationship between the entities may be established, and the various entities stitched together or combined to form a global numerical entity that comprises the full geometry and color representation of the target zone. The larger the overlap zone, the greater the accuracy with which the different zones may be synchronized or stitched together spatially. Where the sub entities include color data of the intraoral cavity 200, the actual stitching technique may be applied to data points corresponding to the hard tissues therein, which have a different color to the soft tissues such as gums, for example as described in the aforesaid co-pending application entitled "METHOD FOR PROVIDING DATA ASSOCIATED WITH THE INTRAORAL CAVITY".

The zones that are scanned should preferably together fully span the target zone T of interest, however it sometimes happens that a part of the target zone is missed out, and thus after the stitching procedure is completed, the global numerical entity thus formed still lacks surface data in some areas. According to the invention, such areas are identified in steps 12' and 13' by the processor 52 which determines that the density of data points in some parts of the entity is below a predetermined value, indicative of a lack of data thereat, for example.

Additionally or alternatively, having provided to the processor 52 the type of procedure for which the numerical entity is required, the processor can analyze the numerical entity in a different manner to determine whether it is sufficiently defined for this purpose. For example, having found quantitatively there is sufficient data, it is now necessary to determine if qualitatively the data is sufficient.

For example, if the numerical entity is to be used in the context of a crown prosthesis, for example as described above for the first aspect of the invention, it is important for the finish line to be well defined. Sometimes, parts of the finish line may be defined on a dental surface that is close to orthogonal with respect to the occlusal plane. If a confocal-type scanner is used at 31 for providing the surface data for this part of finish line, it is possible for the accuracy of definition of the finish line to be diminished the closer to parallel the output face of the scanner is with respect to the occlusal plane. Greater accuracy could be obtained in the scanner is turned to face the aforesaid dental surface close to face-on rather than close to edge-on. Accordingly, the processor 52 may determine whether the definition of the finish line is sufficiently good, and this may be done by comparing the orientation of the scanner 32 with respect to the aforesaid dental surface, according to preset criteria, for example. Thus, in step 13', the processor 52 determines whether data is missing, or whether the accuracy of the data of the numerical entity is insufficient.

In step 14', feedback data is generated to alert the user as to how to correct for the insufficiency of definition. For example, in the case where some surface areas of the entity are missing, the processor 52 first identifies the missing areas for the user, and then may compute the best angle and position for the scanner 31 to scan the intraoral cavity such as to provide the missing surface data. This information may be provided by display 54, for example by providing a graphical image of the entity, with the deficient areas marked hereon, and then arrows or markers with respect thereto showing the desired position of the scanner 31. Of course, it may be that more than one scan is required to make up for the missing data, and the processor provides the required feedback data to deal with each scan.

Similarly, in the case where some surface areas of the entity require better definition, the processor 52 may compute the best angle and position for the scanner 31 to scan the intraoral cavity such as to provide better definition of those areas. This information may also be provided by display 54, for example by providing a graphical image of the entity, and then arrows or markers with respect thereto showing the desired position of the scanner 31. As before, more than one scan may be required to provide the higher accuracy data, and the processor provides the required feedback data to deal with each scan. Other parts requiring special definition may include, for example, undercut zones of the preparation.

Furthermore, the processor may be programmed to alert the user when the entity is sufficiently well defined for the purpose for which it is needed. In such a case, the feedback data is deigned to alert the user that the scan is complete, and may comprise a distinct visual or audio signal, similar but distinguishable from other audio/visual signals provided by display 54, as described herein, mutatis mutandis.

It should be noted that the method 10' according to the second aspect of the invention may be carried out in step 11 (FIG. 1) of the first aspect of the invention, such as to ensure that the entity provided in step 11 is sufficient for steps 12 to 14 thereof.

Thus, in the second aspect of the invention, the feedback data may essentially be used to facilitate the acquisition of data that may be used to construct the numerical entity for subsequent use, for example according to the first aspect of the invention.

According to the first and second aspects of the invention, the entity obtained by scam ling via scanner 31 is displayed in real time via display 54, and when the scanning is complete and acceptable, feedback data is provided alerting the user to this fact.

Further, the present invention, according to the first and second aspects thereof, may be used solely to obtain verification that a particular preparation is in a suitable condition for implanting a prosthesis.

Further, the analysis of the scanned data, whether locally or at a remote site such as for example the service centers 23, dental labs 26, and so on, typically via suitable algorithms, may also use the following parameters: the type of restoration required; patient parameters—age, sex, origin, dental condition (implants in the scanned area, root canals, soft tissue condition, and so on), budget for the procedure, and so on.

In the third aspect of the invention, the feedback data is essentially used in an interactive manner together with a material removing process to facilitate the performance of a procedure with respect to the intraoral cavity.

For example, the process for removing dental material to create the preparation may be effected in a number of stages, at the end of each material removing stage the preparation area being scanned and displayed in real time to guide the dental practitioner as to how to proceed to the next stage, such as to provide an optimal preparation geometry. In particular, when the prosthesis is a bridge, the system guides the practitioner to provide the one of the preparation zones, and then based on this geometry calculates an optimal geometry for the second preparation zone required for the bridge, and correspondingly guides the practitioner accordingly. At each material removing stage, the processor 52 re-evaluates the full picture, and may suggest that the first preparation be modified instead of or in addition to the second preparation.

At least the first aspect of the invention may be used with respect to a positive model of a dentition, in a similar manner to that described above for a real dentition, mutatis mutandis.

While the method of the invention has been described, based on a representation of surface information, the three dimensional entities in the oral cavity, such as for example the teeth gums and so on, and also the 3D entities that are created by the system 50, including the preparation 10, for example, may be described instead by solid representations or any other topographical or geometrical representations.

According to the invention feedback data useful in prosthodontic procedures associated with the intra oral cavity is provided. First, a 3D numerical model of the target zone in the intra oral cavity is provided, and this is manipulated so as to extract particular data that may be useful in a particular procedure, for example data relating to the finish line or to the shape and size of a preparation. The relationship between this data and the procedure is then determined, for example the clearance between the preparation and the intended crown. Feedback data, indicative of this relationship, is then generated, for example whether the preparation geometry is adequate for the particular type of prosthesis.

In the method claims that follow, alphabetic characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

What is claimed is:

1. An intraoral scanning system for scanning an intraoral dental structure of a patient in a dental procedure, the intraoral scanning system comprising:
an intraoral scanner; and
one or more processors coupled to the intraoral scanner and programmed with instructions that when executed by the one or more processors cause the intraoral scanning system to:
build a 3D model of the intraoral dental structure of the patient based on scan data acquired via the intraoral scanner within an intraoral cavity of a patient; and
output feedback on a display, the feedback including highlighting a portion of the 3D model that includes scan data that includes a finish line of the intraoral dental structure, wherein the scan data that includes the finish line indicates that the finish line is not suitable for receiving a prosthetic.

2. The system of claim 1, wherein scan data that includes the finish line of the intraoral dental structure is not suitable for receiving a prosthetic because scan data that includes the finish line of the intraoral dental structure is missing data representing a portion of a surface of the intraoral dental structure.

3. The system of claim 2, wherein the finish line of the intraoral dental structure is missing data at a shoulder of a finish line of the intraoral dental structure.

4. The system of claim 1, wherein the finish line of the intraoral dental structure is not suitable for receiving a prosthetic because the 3D model the intraoral dental structure is missing data representing a portion of the finish line.

5. The system of claim 1, wherein the portion of the 3D model includes an undercut.

6. The system of claim 1, wherein the instructions, when executed by the one or more processors, further cause the intraoral scanning system to:
acquire, via the intraoral scanner, data representing the portion of a surface of the intraoral dental structure that is not suitable for receiving a prosthetic in the 3D model; and
modify the 3D model of the intraoral dental structure of the patient to complete the surface of the intraoral dental structure that is not suitable for receiving a prosthetic.

7. The system of claim 6, wherein the instructions, when executed by the one or more processors, further cause the intraoral scanning system to:
determine that the 3D model is complete; and
provide feedback to a user indicating that the 3D model is complete.

8. The system of claim 7, wherein determining that the 3D model is complete includes determining that the 3D model is sufficiently well defined for a purpose for which the 3D model is needed.

9. The system of claim 1, wherein the scan data comprises at least one numerical entity representative of a three-dimensional surface geometry of a surface of the intraoral dental structure of the patient including a dental preparation and one or more teeth adjacent to the dental preparation, the scan data being generated by scanning a part of an intraoral cavity using the intraoral scanner.

10. The system of claim 1, wherein the feedback includes a scanner position and angle relative to the 3D model for rescanning an area of the 3D model that is deficient comprises a plurality of positions and orientations.

* * * * *